(12) United States Patent
Maddox et al.

(10) Patent No.: US 8,809,447 B2
(45) Date of Patent: *Aug. 19, 2014

(54) ACETOACETATE-FUNCTIONAL MONOMERS AND THEIR USES IN COATING COMPOSITIONS

(75) Inventors: John Thorton Maddox, Jonesborough, TN (US); Stacey James Marsh, Church Hill, TN (US)

(73) Assignee: Eastman Chemical Company, Kingsport, TN (US)

( * ) Notice: Subject to any disclaimer, the term of this patent is extended or adjusted under 35 U.S.C. 154(b) by 616 days.

This patent is subject to a terminal disclaimer.

(21) Appl. No.: 12/968,849

(22) Filed: Dec. 15, 2010

(65) Prior Publication Data

US 2012/0157610 A1 Jun. 21, 2012

(51) Int. Cl.
C09D 5/02 (2006.01)
C07C 69/72 (2006.01)
C09D 133/14 (2006.01)
C08F 220/28 (2006.01)

(52) U.S. Cl.
CPC .............. *C07C 69/72* (2013.01); *C07C 2101/14* (2013.01); *C09D 133/14* (2013.01); *C08F 2220/283* (2013.01); *C07C 2101/04* (2013.01); *C09D 5/02* (2013.01)
USPC ........... 524/558; 524/559; 524/560; 524/561; 524/562; 526/309; 526/321; 526/322; 526/323; 526/323.1; 526/323.2; 560/174

(58) Field of Classification Search
CPC ........ C09D 5/02; C09D 133/14; C07C 69/72; C07C 2101/04; C07C 2101/14; C08F 2220/283
USPC .......... 524/558, 559, 560, 561, 562; 526/321, 526/322, 323, 323.1, 323.2; 560/174
See application file for complete search history.

(56) References Cited

U.S. PATENT DOCUMENTS

| | | | |
|---|---|---|---|
| 3,197,500 A | 7/1965 | Kitchens et al. | |
| 3,214,461 A | 10/1965 | Elam et al. | |
| 3,220,865 A | 11/1965 | Coney | |
| 3,892,903 A | 7/1975 | Dowbenko | |
| 4,215,195 A | 7/1980 | Ponticello et al. | |
| 4,839,413 A | 6/1989 | Kiehlbauch et al. | |
| 4,855,349 A | 8/1989 | Ingle | |
| 4,927,876 A | 5/1990 | Coogan et al. | |
| 4,939,233 A | 7/1990 | Jenkins et al. | |
| 4,946,932 A | 8/1990 | Jenkins | |
| 5,055,506 A | 10/1991 | Knutson | |
| 5,073,445 A | 12/1991 | Ingle | |
| 5,137,961 A | 8/1992 | Goos et al. | |
| 5,155,252 A * | 10/1992 | Yamamoto et al. | 560/190 |
| 5,247,040 A | 9/1993 | Amick et al. | |
| 5,296,530 A | 3/1994 | Bors et al. | |
| 5,349,026 A | 9/1994 | Emmons et al. | |
| 5,391,624 A | 2/1995 | Rasoul et al. | |
| 5,484,849 A | 1/1996 | Bors et al. | |
| 5,494,975 A | 2/1996 | Lavoie et al. | |
| 5,498,659 A | 3/1996 | Esser | |
| 5,519,071 A * | 5/1996 | Rheinberger et al. | 523/116 |
| 5,534,310 A | 7/1996 | Rokowski et al. | |
| 5,539,073 A | 7/1996 | Taylor et al. | |
| 5,721,329 A | 2/1998 | Fujiwa et al. | |
| 5,756,826 A | 5/1998 | Hanselmann | |
| 5,820,993 A | 10/1998 | Schall et al. | |
| 5,872,297 A | 2/1999 | Trumbo | |
| 5,886,116 A | 3/1999 | Trumbo | |
| 5,889,098 A | 3/1999 | Trumbo | |
| 5,932,350 A | 8/1999 | Lauer et al. | |
| 5,945,489 A | 8/1999 | Moy et al. | |

(Continued)

FOREIGN PATENT DOCUMENTS

EP 0 241 127 A2 10/1987
EP 0 492 847 A2 7/1992

(Continued)

OTHER PUBLICATIONS

Moszner, Norbert et al., "Reaction behavior of β-ketoesters: 3. Polymerizable reaction products of 2-acetoacetoxyethyl methacrylate with aromatic isocyanates and aldehydes", Polymer Bulletin 33, (1994), 43-49.

Witzman, J. S., et al., "Comparison of Methods for the Preparation of Acetoacetylated Coating Resins", Eastman Kodak Company, Oct. 1990, vol. 62, No. 789 Presented at the 16th Annual Water-Borne and Higher-Solids Coatings Symposium, New Orleans, LA, Feb. 1-3, 1989.

Smith, Oliver W., et al., "New vinyl monomers for emulsion polymers", Progress in Organic Coatings, 22, (1993), pp. 19-25.

(Continued)

*Primary Examiner* — Peter D Mulcahy
(74) *Attorney, Agent, or Firm* — James K. Leonard

(57) ABSTRACT

Acetoacetate-functional monomers are disclosed that correspond to the following formula 1:

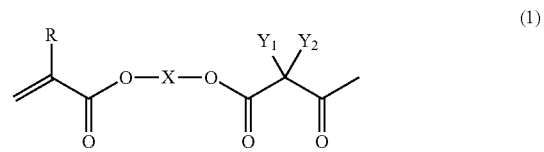

(1)

in which R is hydrogen, or a methylgroup; X is a branched alkyl or a branched cyclic alkyl having from 5 to 8 carbon atoms; and Y1 and Y2 are independently hydrogen or methyl. Also disclosed are emulsion, suspension, and solution polymers comprising residues from the acetoacetate-functional monomer of formula 1 and one or more additional ethylenically unsaturated monomers. Self-curing coating compositions are likewise disclosed that comprise the acetoacetate-functional monomer of formula 1, and optionally one or more additional ethylenically unsaturated monomers. Latex formulations are also disclosed that comprise a polymer having residues from the acetoacetate-functional monomer of formula 1 dispersed in an evaporable aqueous carrier.

10 Claims, No Drawings

(56) References Cited

U.S. PATENT DOCUMENTS

| | | |
|---|---|---|
| 5,962,556 A | 10/1999 | Taylor |
| 5,985,018 A | 11/1999 | Link et al. |
| 5,990,224 A | 11/1999 | Raynolds et al. |
| 5,998,543 A | 12/1999 | Collins et al. |
| 6,005,035 A | 12/1999 | Raynolds et al. |
| 6,025,410 A | 2/2000 | Moy et al. |
| 6,060,556 A | 5/2000 | Collins et al. |
| 6,090,882 A | 7/2000 | Trumbo |
| 6,201,048 B1 | 3/2001 | Raynolds et al. |
| 6,262,169 B1 | 7/2001 | Helmer et al. |
| 6,265,028 B1 | 7/2001 | Zhao et al. |
| 6,417,267 B1 | 7/2002 | Stockl et al. |
| 6,417,269 B1 | 7/2002 | Murray et al. |
| 6,969,734 B1 | 11/2005 | Pressley et al. |
| 7,101,921 B2 | 9/2006 | Edwards et al. |
| 7,138,438 B2 | 11/2006 | Lauer et al. |
| 2003/0134973 A1 | 7/2003 | Chen et al. |
| 2008/0194722 A1 | 8/2008 | Abuelyaman et al. |
| 2010/0081769 A1 | 4/2010 | Ma |

FOREIGN PATENT DOCUMENTS

| | | |
|---|---|---|
| EP | 0 501 614 A2 | 9/1992 |
| EP | 0 875 496 A1 | 11/1998 |
| EP | 1 070 699 A1 | 1/2001 |
| EP | 1 348 416 A1 | 10/2003 |
| GB | 2 335 424 A | 9/1999 |
| JP | 4041462 A | 2/1992 |
| JP | 4106925 A | 4/1992 |
| JP | 05273799 A | 10/1993 |
| JP | 06027750 A | 2/1994 |
| JP | 06095441 A | 4/1994 |
| JP | 06130706 A | 5/1994 |
| JP | 07084379 A | 3/1995 |
| JP | 08050380 A | 2/1996 |
| JP | 08194341 A | 7/1996 |
| JP | 11335222 A | 12/1999 |
| JP | 3274214 B2 | 4/2002 |
| JP | 2003 237246 A | 8/2003 |
| JP | 3505129 B2 | 3/2004 |
| JP | 2004 125985 A | 4/2004 |
| JP | 3588014 B2 | 11/2004 |
| WO | WO 99/58608 A1 | 11/1999 |
| WO | WO 2005/105963 A1 | 11/2005 |
| WO | WO 2007/094922 A2 | 8/2007 |

OTHER PUBLICATIONS

Moszner, Norbert, et al., "Reaction behavior of monomeric β-ketoesters: 2. Synthesis, characterization and polymerization of methacrylate group containing enamines", Polymer Bulletin 32, (1994) pp. 419-426.

ASTM D2369.

Notification of Transmittal of The International Search Report and the Written Opinion of the International Searching Authority, or the Declaration dated Feb. 14, 2012, International application No. PCT/US2011/0162181.

Notification of Transmittal of The International Search Report and the Written Opinion of the International Searching Authority, or the Declaration dated Feb. 9, 2012, International application No. PCT/US2011/062295.

Notification of Transmittal of the International Search Report and the Written Opinion of the International Searching Authority, or the Declaration with a mailing date of Feb. 29, 2012 and International application No. PCT/US2011/063903.

Copending U.S. Appl. No. 12/968,816, filed Dec. 15, 2010, John Thornton Maddox, et al.

Copending U.S. Appl. No. 12/968,780, filed Dec. 15, 2010, John Thornton Maddox, et al.

Office Action dated Aug. 5, 2011 in copending U.S. Appl. 12/968,816.

Office Action dated Jun. 7, 2012 in copending U.S. Appl. 12/986,816.

Office Action dated Oct. 3, 2012 in copending U.S. Appl. 12/986,816.

* cited by examiner

ACETOACETATE-FUNCTIONAL MONOMERS AND THEIR USES IN COATING COMPOSITIONS

FIELD OF THE INVENTION

This invention relates to ethylenically unsaturated, hydrolytically-stable monomers, and in particular, to hydrolytically-stable, acetoacetate-functional monomers and their uses in coating compositions.

BACKGROUND OF THE INVENTION

Waterborne acrylic coatings can deliver performance comparable to traditional solvent-borne coatings while meeting increasingly stringent coating VOC emission regulations. Acetoacetoxyethyl methacrylate (AAEM) is a functional monomer used to make self-crosslinking, room-temperature-cure emulsion copolymers that may be used to produce coatings having good hardness and chemical and block resistance. Once incorporated into the copolymer, the acetoacetoxy-functionality of the AAEM monomer can cross-link via an "oxidative cure" or react with an added cross-linker such as a diamine to produce a cured film.

One of the recognized drawbacks of the acetoacetoxy moiety of AAEM is that it is known to be hydrolytically labile and a decline in film performance of copolymers prepared from this monomer has been correlated with the heat history and age of the copolymers. To avoid this degradation in performance, manufacturers have added volatile amines to convert the acetoacetate to its enamine tautomer and limit the hydrolysis. While this slows the hydrolysis, it does not completely eliminate it. Additionally, the addition of a volatile amine component can introduce a disagreeable odor to the coating product during application.

U.S. Pat. No. 4,215,195 to Ponticello et al. discloses compounds, including methacrylamides and acetoacetamidoethyl methacrylate, that can be homopolymerized or copolymerized with each other or with polymerizable ethylenically unsaturated monomers to give crosslinkable polymers. Polymers made from monomers having amide functionality are said to exhibit improved hydrolytic stability.

U.S. Pat. Nos. 4,855,349 and 5,073,445 to Ingle disclose permanently flexible and non-tacky coating mastic and caulking compositions that contain one or more polymers having a $T_g$ of about $-50°$ C. to about $-10°$ C. and pendant functional groups attached to the polymer backbone having the formula $—R_1—C=O—CH2-X$, in which $R_1$ is a divalent organic radical at least 3 atoms in length, and X is organoacyl or cyano. Acetoacetoxy-ethyl methacrylate is exemplified.

U.S. Pat. No. 5,296,530 to Bors et al. discloses a method for light-assisted curing of coatings by providing coatings with an enamine content sufficient to enhance the cure rate of the coatings. According to the disclosure, a quick-curing coating is prepared from a polymer having acetoacetyl groups, in which substantially all of the acetoacetyl groups have been converted to enamine functionality, for example by treatment with ammonia or primary amine. Coatings which are so prepared are said to cure more quickly under sunlight or ultraviolet light than coatings which contain the acetoacetyl functional polymer which has not been converted to enamine. Acetoacetoxy-ethyl methacrylate is exemplified.

U.S. Pat. No. 5,494,975 to Lavoie et al. discloses the preparation of polymers containing functional acetoacetate groups and then, following the polymerization, reacting the acetoacetate group with a functional amine to form an enamine. A preferred monomer is acetoacetoxyethyl methacrylate. Examples of other monomers said to be useful for introduction of acetoacetate functionality include acetoacetoxyethyl acrylate, acetoacetoxypropyl methacrylate, allyl acetoacetate, acetoacetoxybutyl methacrylate, and 2,3-di(acetoacetoxy)propyl methacrylate.

U.S. Pat. No. 5,484,849 to Bors et al. discloses air curing polymer compositions which contain an acetoacetate-functional polymer and an autoxidizable material. The compositions cure on exposure to oxygen. The acetoacetate-functional polymers can be prepared by means known in the art. A preferred method is polymerization through incorporation which includes an acetoacetate-functional monomer, with acetoacetoxy-ethyl methacrylate, acetoacetoxypropyl methacrylate, and allyl acetoacetate being exemplified. Examples of other monomers said to be useful include acetoacetoxyethyl acrylate, acetoacetoxybutyl methacrylate, and 2,3-di(acetoacetoxy)propyl methacrylate.

J. Stewart Witzeman et al. reported that acetoacetylated polymers and resins have been shown to be capable of undergoing a variety of crosslinking reactions, and that the best industrial method for acetoacetylation of monomeric and polymeric materials is by transesterification with t-butyl acetoacetate. They also reported that among the processes which have been used to effect crosslinking of acetoacetylated polymeric materials are reactions with diamines, melamine, aldehydes, isocyanates, chelation with metals, and Michael reaction with activated olefins. They further reported that acetoacetylated materials can be prepared by treating a nucleophile with diketene, from the thermal reaction of 2,2,6-trimethyl-4H-1,3,-dioxin-4-one, TKD, the diketene-acetone adduct, or by transesterification with another acetoacetate. See *Comparison of Methods for the Preparation of Acetoacetylated Coating Resins*, Witzeman, J. S.; Dell Nottingham, W.; Del Rector, F. J. Coatings Technology; Vol. 62, 1990, 10 1.

U.S. Pat. No. 5,756,826 to Hanselmann discloses a process for preparing acetoacetates, in which (2-acetoacetamido-2-methylpropyl)methacrylate may be formed by reacting 2-amino-2-methyl-1-propanol with diketene, the adduct then being reacted with thiodiphenylamine and methacrylic anhydride, followed by further thiodiphenylamine to form the (2-acetoacetamido-2-methylpropyl)methacrylate. Alternatively, the reaction may be carried out in a similar method, but using different alcohols.

U.S. Pat. No. 5,872,297 to Trumbo discloses ethylenically-unsaturated 1,3-diketoamide functional compounds, polymers comprised thereof, and latex formulations containing polymeric ingredients having 1,3-diketoamide functional pendant moieties. The 1,3-diketoamide functional pendant moieties are said to have excellent hydrolytic stability.

U.S. Pat. Nos. 5,945,489 and 6,025,410 to Moy et al. disclose liquid oligomeric compositions made by the Michael addition reaction of acetoacetate functional donor compounds with multifunctional acrylate receptor compounds where the equivalent ratios of multifunctional acrylate to acetoacetate vary from greater than or equal to 1:1 to greater than or equal to 13.2:1, depending on the functionality of both multifunctional acrylate and acetoacetate. The use of multifunctional (diacrylates, triacrylates, and tetraacrylates) acrylates results in residual unsaturation in the oligomers that is useful for subsequent cross-linking. The liquid oligomers may thus be further crosslinked to make coatings, laminates and adhesives.

U.S. Pat. No. 5,990,224 to Raynolds et al. discloses low foam waterborne polymer compositions stabilized against gelling due to the addition of a poly(alkylenimine) by addition of surfactants. Enamine-functional polymers are said to represent a preferred embodiment of polymers, and may be prepared by reacting a polymer having acetoacetoxy groups with ammonia or a primary or secondary amine, such as polyethylenimine, (PEI). Acetoacetoxy-type functional polymers are said to be useful, and may be prepared by free radical emulsion polymerization of vinyl monomers having an acetoacetoxy functionality with other vinyl monomers. Preferred monomers of this type are said to include acetoacetoxy-ethyl methacrylate, acetoacetoxyethyl acrylate, acetoacetoxy(methyl)ethyl acrylate, acetoacetoxypropyl acrylate, allyl acetoacetate, acetoacetamido-ethyl(meth)acrylate, and acetoacetoxybutyl acrylate, with acetoacetoxyethyl methacrylate (AAEM) representing a particularly preferred such monomer. Acetoacetoxyethyl methacrylate is the monomer used in the examples.

U.S. Pat. No. 5,962,556 to Taylor discloses the use of a monomer represented by formula:

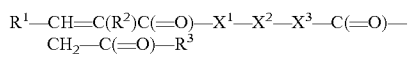

where $R^1$ is a hydrogen or halogen; $R^2$ is a hydrogen, halogen, $C_1$-$C_6$ alkylthio group, or $C_1$-$C_6$ alkyl group; $R^3$ is a $C_1$-$C_6$ alkyl group; $X^1$ and $X^3$ are independently O, S or a group of the formula: —N($R^1$)—, where $R^1$ is a $C_1$-$C_6$ alkyl group; $X^2$ is a $C_2$-$C_{12}$ alkylene group or $C_3$-$C_{12}$ cycloalkylene group. The alkyl and alkylene group described may be straight or branched. Preferred monomers are said to include acetoacetoxyethyl(meth)acrylate, acetoacetoxy(methyl)ethyl(meth)acrylate, acetoacetoxypropyl(meth)acrylate and acetoacetoxybutyl(meth)acrylate, with the term "(meth)acrylate" used in the patent to denote methacrylate or acrylate. The only such monomer exemplified is acetoacetoxyethyl methacrylate. U.S. Pat. No. 6,262,169 to Helmer et al., and U.S. Pat. Publn. No. 2003/0134973A1 to Chen et al., likewise disclose polymers having acetoacetoxy functional groups.

GB 2 335 424A, related to curable compounds and polymers having reactive functional groups, discloses an unsaturated compound (A), that can be 2-aceto-acetoxyethyl methacrylate, 3-acetoacetoxypropyl methacrylate, allyl acetoacetate, or an acetoacetate of a polyol such as trimethylol propane or pentaerythritol, reacted with a compound (B) which can be inter alia an acrylate for example having epoxide functionality, an acrylamide, or a maleate diester, to obtain a compound that can, itself, be used as a monomer, or further reacted with another compound having an activated double bond. For example, according to the disclosure, acetoacetoxyethyl methacrylate is reacted with glycidyl acrylate to produce bis(carboglycidoxyethyl)acetoacetoxyethyl methacrylate, and dimethyl malonate is reacted with neopentyl glycol to produce a neopentyl malonate polyester. A further disclosure is trimethylolpropane reacted with t-butyl acetoacetate to form 1,1,1-tris(acetoacetoxymethyl)propane.

U.S. Pat. Publn. No. 2008/0194722 discloses a hardenable dental composition that includes a polymerizable compound having at least one cyclic allylic sulfide moiety and at least one (meth)acryloyl moiety. The polymerizable compound is referred to as a hybrid monomer or a hybrid compound, and can be a substituted acetoacetoxyethyl methacrylate. See Formula 1a-5. The hardenable component is one that is capable of polymerization and/or crosslinking reactions including, for example, photopolymerization reactions and chemical polymerization techniques (e.g., ionic reactions or chemical reactions forming radicals effective to polymerize ethylenically unsaturated compounds, (meth)acrylate compounds, etc.) involving one or more compounds capable of hardening. Hardening reactions are also said to include acid-base setting reactions such as those common for cement forming compositions (e.g., zinc polycarboxylate cements, glass-ionomer cements, etc.).

U.S. Pat. Publn. No. 2010/0081769 discloses a process for producing a linear block copolymer, useful as a dispersant for pigment, wherein the block copolymer comprises acetoacetyl amine functional groups which serve as pigment anchoring groups. The acetoacetyl amine functional groups can be formed by reacting hydroxyl functional groups with an acetoacetate agent, and then reacting the resulting acetoacetate functional groups with a primary amine. One example of ethylenically unsaturated acetoacetate monomers that is useful for introduction of acetoacetate functional group into the block copolymer can be acetoacetoxyethyl methacrylate. Examples of other monomers that can be used to introduce an acetoacetate functional group into the block copolymer can include acetoacetoxyethyl acrylate, acetoacetoxypropyl methacrylate, acetoacetoxypropyl acrylate, allyl acetoacetate, acetoacetoxybutyl methacrylate, acetoacetoxybutyl acrylate, and the like.

Though acetoacetoxy-functional monomers are known to be useful in polymerization processes, and the polymers and copolymers made from such processes find use in coating compositions, there remains a need in the art for monomers useful in coating compositions, whether UV-curable monomer mixtures, solution acrylics, or emulsion polymers known as latexes, and that may be used to produce coatings having good hardness and chemical and block resistance, and that exhibit improved hydrolytic stability.

SUMMARY OF THE INVENTION

In one aspect, the invention relates to acetoacetate-functional monomers that correspond to the following formula 1:

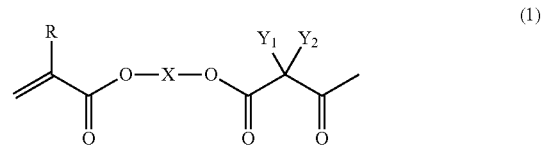

in which R is hydrogen, or a methyl group; X is a branched alkyl or a branched cyclic alkyl having from 5 to 8 carbon atoms; and Y1 and Y2 are independently hydrogen or methyl. In another aspect, R is hydrogen or methyl; X is a branched alkyl having from 5 to 8 carbon atoms; and Y1 and Y2 are hydrogen. In yet another aspect, R may be methyl; X a branched cyclic alkyl; and Y1 and Y2 hydrogen. In yet another aspect, R may be methyl; X dimethylpropyl; and Y1 and Y2 hydrogen.

In a further aspect, the invention relates to an ethylenically unsaturated acetoacetate-functional monomer that corresponds to the following structure:

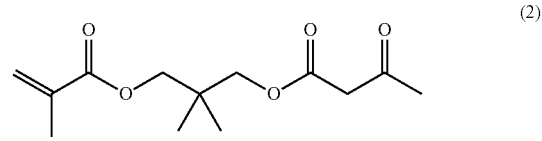 [SMILES: C=C(C)C(=O)OCC(C)(C)COC(=O)CC(C)=O]

In yet another aspect, the invention relates to an ethylenically unsaturated acetoacetate-functional monomer that corresponds to the following structure:

In yet another aspect, the invention relates to an ethylenically unsaturated acetoacetate-functional monomer that corresponds to either of the following two isomers, or mixtures thereof:

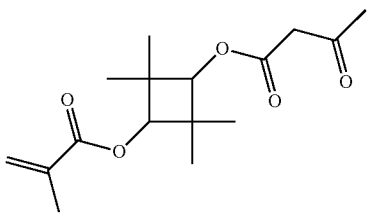

(3)

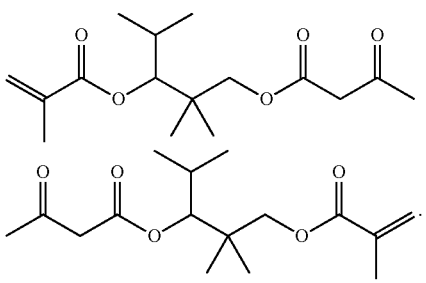

(4)

In a further aspect, the invention relates to an ethylenically unsaturated acetoacetate-functional monomer that corresponds to the following structure:

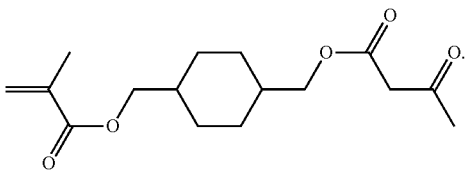

(5)

In yet another aspect, the invention relates to emulsion polymers comprising residues from the acetoacetate-functional monomer of formula 1 and one or more additional ethylenically unsaturated monomers. In a further aspect, the one or more additional ethylenically unsaturated monomers may comprise one or more of: methyl(meth)acrylate, ethyl(meth)acrylate, propyl(meth)acrylate, isopropyl(meth)acrylate, butyl(meth)acrylate, isobutyl(meth)acrylate, hexyl(meth)acrylate, isooctyl(meth)acrylate, isodecyl(meth)acrylate, lauryl(meth)acrylate, stearyl(meth)acrylate, phenoxyethyl(meth)acrylate, methoxyethyl(meth)acrylate, benzyl(meth)acrylate, ethoxyethyl(meth)acrylate, 2-ethylhexyl(meth)acrylate, cyclopentyl(meth)acrylate, isobutyl(meth)acrylate, styrene, p-methyl styrene, o-methyl styrene, p-butyl styrene, or alpha-methyl styrene.

In yet another aspect, the invention relates to solution polymers comprising residues from the acetoacetate-functional monomer of formula 1, and in another aspect, the invention relates to self-curing coating compositions that comprise the acetoacetate-functional monomer of claim 1, and that optionally include one or more additional ethylenically unsaturated monomers.

In yet a further aspect, the invention relates to latex formulations comprising a polymer having residues from the acetoacetate-functional monomer of formula 1 dispersed in an evaporable aqueous carrier.

Other aspects of the invention are as set forth herein.

DETAILED DESCRIPTION OF THE INVENTION

In one aspect, the invention relates to ethylenically unsaturated, acetoacetate-functional monomers useful in coating compositions.

In one aspect, the ethylenically unsaturated, acetoacetate-functional monomers correspond to the following formula 1:

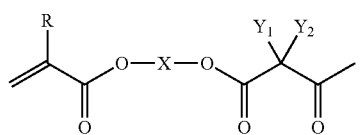

(1)

in which R is hydrogen, or a methyl group;
X is a branched alkyl or a branched cyclic alkyl having from 5 to 8 carbon atoms;
and Y1 and Y2 are independently hydrogen or methyl.

In another aspect, the invention relates to acetoacetate-functional monomers, useful for preparing coating compositions, that correspond to formula 1 above, wherein R is hydrogen or methyl; X is a branched alkyl having 5 to 8 carbon atoms; and Y1 and Y2 are hydrogen or methyl.

In yet another aspect, the invention relates to acetoacetate-functional monomers, useful for preparing coating compositions, that correspond to formula 1 above, wherein R is methyl; X is dimethylpropyl; and Y1 and Y2 are hydrogen.

In yet another aspect, the invention relates to acetoacetate-functional monomers, useful for preparing coating compositions, that correspond to formula 1 above, wherein R is methyl; X is 2,2,4,4-tetramethylcyclobutyl; and Y1 and Y2 are hydrogen.

In yet another aspect, the invention relates to acetoacetate-functional monomers, useful for preparing coating compositions that correspond to formula 1 above, wherein R is methyl, X is selected from dimethylpropyl, 2,2,4-trimethylpentyl, and 2,2,4,4-tetramethylcyclobutyl, and Y1 and Y2 are hydrogen.

When we say that X is a branched alkyl or a branched cyclic alkyl having from 5 to 8 carbon atoms, we mean, for example, that X may be a straight chain alkyl, such that, in the case of propyl having at least two additional carbons branching from the propyl group, for example, the branches may be dimethyl, or a single ethyl group, or trimethyl or diethyl, for example. If the X group is a longer straight chain alkyl, then the number of carbons branching from the group will be fewer. For example, if X is a branched pentyl, then the carbons in the branching will be 3 or less, for example methyl, ethyl, dimethyl, or one methyl and one ethyl group, for example. X may also be a branched cyclic alkyl, such that, in the case of cyclobutyl, the number of carbons branching from the cyclic alkyl will be 4 or less, for example methyl, ethyl, dimethyl, or trimethyl. If the branched cyclic alkyl is cyclohexyl, for example, then the number of carbons branching from the cyclohexyl will be one or two, for example, methyl, ethyl, or dimethyl. We have found that the acetoacetate-functional monomers of the invention having a branched alkyl or a branched cyclic alkyl having from 5 to 8 carbon atoms in place of the ethyl group in AAEM, results in monomers having increased hydrolytic stability, a known drawback of using AAEM itself. Certain 3-oxopentanoate monomers also exhibiting improved hydrolytic stability are being separately pursued in a copending patent application filed on the same date herewith.

In yet another aspect, the invention thus relates to monomers, that is, simply to the molecules themselves, and specifically to 3-(methacryloyloxy)-2,2-dimethylpropyl 3-oxobutanoate, 3-(methacryloyloxy)-2,2,4,4-tetramethylcyclobutyl 3-oxobutanoate, either of the following two isomers, 3-(methacryloyloxy)-2,2,4-trimethylpentyl 3-oxobutanoate or 1-(methacryloyloxy)-2,2,4-trimethylpentan-3-yl 3-oxobutanoate or mixtures thereof, and (4-(methacryloyloxymethyl)cyclohexyl)methyl 3-oxobutanoate, having, respectively, the following structures:

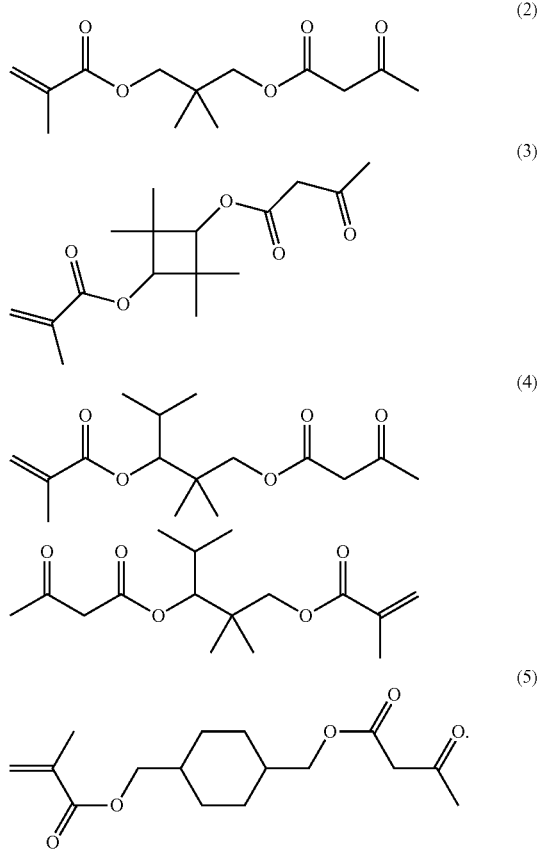

In yet another aspect, the invention relates to homopolymers and copolymers of the above-referenced monomers, for example made using emulsion polymerization or solution acrylic processes, that are useful as or in coating compositions, for example to make UV curable compositions possessing hydrolytic stability.

In yet another aspect, the invention relates to one or more of the above-referenced monomers, alone or with other known ethylenically unsaturated, or vinyl, monomers, that serve as coating compositions by being readily polymerized via UV-cure. These mixtures may include an organic solvent, or may simply be mixtures of the monomers themselves, that cure upon exposure to air with or without the use of initiators.

Thus, the invention is also directed to polymers derived from at least one of the acetoacetate-functional monomers set out herein. The polymer may be a homopolymer, or a copolymer of the monomer and one or more additional copolymerizable monomers. The polymer may be a solution polymer, or may alternatively be a latex formed via emulsion polymerization, as set forth herein.

The polymers according to the invention are derived from the acetoacetate-functional monomers of the invention, and are addition polymers formed via a free-radical addition polymerization. In such addition polymers, the propagating species may be a free radical, and the polymer is formed in a chain-growth fashion polymerization as understood in the art. As noted, these polymers may be solution polymers, in which the monomers are polymerized in an inert solvent via a free-radical polymerization. Alternatively, the polymers may be latex polymers in which a monomer solution is emulsified in an aqueous solution, and under agitation is reacted via a free-radical polymerization process as described herein, to form latex particles. In a further alternative, the polymers may be suspension polymers, in which the monomers are suspended in a continuous aqueous phase, the suspension polymers being most easily distinguished from the latex particles by particle size and intended use. In yet another alternative, the acetoacetate-functional monomers of the invention may be directly applied as a coating composition, alone or with other ethylenically-unsaturated monomers, with a free radical initiator, and free-radical polymerized to form a coating.

The present invention is thus also directed to latex formulations containing a polymer having acetoacetate-functional pendant moieties derived from the acetoacetate-functional monomers of the invention, dispersed in an evaporable aqueous carrier. The acetoacetate-functional monomers employed in the polymers and latex formulations of this invention advantageously exhibit excellent hydrolytic stability so that such formulations can be stored for long periods of time without degradation of the acetoacetate-functional functionality. Additionally, the acetoacetate-functional monomers employed in the polymers and latex formulations of this invention advantageously exhibit the ability to crosslink via a self-curing "oxidative cure", react with an added cross-linker such as a diamine, or cure using ultraviolet light with or without the addition of photoinitiators.

Ethylenically Unsaturated Acetoacetate-Functional Monomers

The monomers of the present invention are characterized as being ethylenically unsaturated monomers that can participate in addition polymerization reactions, alone or with other ethylenically unsaturated monomers. As used herein, ethylenically unsaturated monomers are also described as vinyl monomers, and with respect to the solution polymers, the suspension polymers, and the latex or emulsion polymers described herein, vinyl monomers and ethylenically unsaturated monomers shall be considered interchangeable terms. The polymers made from such monomers are thus addition polymers, and may be formed as solution acrylic polymers, as suspension polymers, or as emulsion polymers, also known as latexes. Alternatively the monomers of the present invention may be provided alone, or as monomer mixtures, and may serve as coating compositions which, once applied, cure to form a coating, as further set out herein.

The ethylenically unsaturated acetoacetate-functional monomers of the invention may be prepared, for example, by reacting a suitable glycol with a diketene delivering reagent such as t-butyl acetoacetate or the diketene-acetone adduct TKD to install the 3-oxobutanoate moiety followed by reaction with a reagent such as methacrylic anhydride to install the ethylenically unsaturated moiety. Alternatively, the ethylenically unsaturated acetoacetate-functional monomers of the invention may be prepared by first reacting a suitable glycol with a reagent such as methacrylic anhydride to install the ethylenically unsaturated moiety followed by reaction with diketene or a diketene delivering agent such as t-butyl acetoacetate or the diketene-acetone adduct TKD to install the 3-oxobutanoate moiety.

When we say that the polymers according to the invention have pendant moieties, we mean that the ethylenically unsaturated monomers of the invention have been reacted into an addition polymer, and that a portion of the monomers remains as a pendant moiety. Alternatively, we may say that the polymers according to the invention have residues from the ethylenically unsaturated monomers of the invention, in which case we mean that the monomers have been reacted into an addition polymer via their ethylenic unsaturation, and that a portion of the monomers remains as a residue. Both these descriptions are well-known in the art of addition polymers, and the descriptions are not otherwise intended to be especially limiting.

When we say that the monomers of the invention are useful in coating compositions, we do not intend this phrase to be especially limiting. For example, we mean that they may be used alone or with other ethylenically unsaturated monomers to form monomer solutions that readily polymerize under desired conditions. Alternatively, the monomers of the invention may be used alone or together with other ethylenically unsaturated monomers to form addition polymers, whether as solution acrylics or emulsion polymers known as latexes.

Emulsion Polymers Made from the Ethylenically Unsaturated Acetoacetate-Functional Monomers In one aspect, the invention thus relates to emulsion polymers containing the inventive monomers of the invention, which are also known as latexes. In these latexes, the polymers formed may have a particle size ranging, for example, from about 80 to about 300 nm, or from 100 nm to 250 nm, or from 125 nm to 200 nm. The $T_g$ of such latexes may range, for example, from about 0° C. to about 80° C., or from 15° C. to 60° C., or from 20° C. to 40° C.

The latex polymer compositions in accordance with the present invention may be prepared by an emulsion or suspension free radical polymerization of ethylenically unsaturated monomers that include the acetoacetate-functional monomers of the invention. These latex polymers may be homopolymers, or may be copolymers of the acetoacetate-functional monomers of the invention and other ethylenically unsaturated monomers.

Examples of other ethylenically unsaturated comonomers include, but are not limited to, acrylic and methacrylic acid esters such as methyl(meth)acrylate, ethyl(meth)acrylate, propyl(meth)acrylate, isopropyl(meth)acrylate, butyl(meth)acrylate, isobutyl(meth)acrylate, hexyl(meth)acrylate, isooctyl(meth)acrylate, isodecyl(meth)acrylate, lauryl(meth)acrylate, stearyl(meth)acrylate, phenoxyethyl(meth)acrylate, methoxyethyl(meth)acrylate, benzyl(meth)acrylate, ethoxyethyl(meth)acrylate, 2-ethylhexyl(meth)acrylate, cyclopentyl(meth)acrylate and isobutyl(meth)acrylate, as well as combinations of these monomers. A combination of these monomers may be used in order to achieve an appropriate Tg or other properties for the functional latex polymer.

Such acrylic and methacrylic acid esters having a C1-C20 alcohol moiety are commercially available or can be prepared by known esterification processes. The acrylic and methacrylic acid ester may contain additional functional groups, such as, hydroxyl, amine, halogen, ether, carboxylic acid, amide, nitrile, and alkyl group. Such esters include carbodiimide(meth)acrylate, methyl(meth)acrylate, ethyl(meth)acrylate, butyl(meth)acrylate, isobutyl(meth)acrylate, ethylhexyl(meth)acrylate, octyl(meth)acrylate, isobutyl(meth)acrylate, allyl(meth)acrylate, and glycidyl(meth)acrylate.

Additional suitable copolymerizable ethylenically unsaturated monomers include styrenic monomers. Styrenic monomers include styrene, as well as substituted styrenes such as C1-C6 alkyl ring-substituted styrene, C1-C3 alkyl alpha-substituted styrene or a combination of ring and an alpha-alkyl substituted styrene. Such styrenic copolymerizable monomers include styrene, p-methyl styrene, o-methyl styrene, p-butyl styrene, alpha-methyl styrene, and combinations thereof.

In addition, vinyl esters may be used as copolymerizable ethylenically unsaturated monomers, including vinyl esters of vinyl alcohol such as the VEOVA series available from Shell Chemical Company as VEOVA 5, VEOVA 9, VEOVA 10, and VEOVA 11 products. See O. W. Smith, M. J. Collins, P. S. Martin, and D. R. Bassett, Prog. Org. Coatings 22, 19 (1993).

In general, the vinyl monomers may be polymerized by a conventional suspension or emulsion free-radical initiated polymerization technique. The polymerization can be initiated by a water-soluble or water-dispersible free-radical initiator, optionally in combination with a reducing agent, at an appropriate temperature, for example from 55 to 90° C. The polymerization of the monomers may be conducted batch wise, semi-batch or in a continuous mode.

A conventional surfactant or a combination of surfactants may be used such as anionic or non-ionic emulsifier in the suspension or emulsion polymerization to prepare a polymer of the invention. Examples of such surfactants include, but are not limited to, alkali or ammonium alkylsulfate, alkylsulfonic acid, or fatty acid, oxyethylated alkylphenol, or any combination of anionic or non-ionic surfactant. A surfactant monomer may be used such as HITENOL HS-20 (which is a polyoxyethylene alkylphenyl ether ammonium sulfate available from DKS International, Inc., Japan). A list of surfactants is available in the treatise: McCutcheon's Emulsifiers & Detergents, North American Edition and International Edition, MC Publishing Co., Glen Rock, N.J. 1993. The amount of the surfactant used is usually between 0.1 to 6 wt %, based on the total weight of the monomers.

As polymerization initiators, any conventional free-radical initiator may be used such as hydrogen peroxide, t-butylhydroperoxide, ammonium or alkali sulfate, di-benzoyl peroxide, lauryl peroxide, di-tertiarybutylperoxide, 2,2'-azobisisobutyronitrile, benzoyl peroxide, and the like. The amount of the initiator is typically between 0.05 to 6.0 wt %, based on the total weight of the total monomers.

A free-radical initiator may be combined with a reducing agent to form a redox initiating system. Suitable reducing agents are those which increase the rate of polymerization and include, for example, sodium bisulfite, sodium hydrosulfide, sodium, ascorbic acid, isoascorbic acid and mixtures thereof. The redox initiating system can be used at similar levels as the free-radical initiators.

In addition, in combination with the initiators and reducing agents, polymerization catalysts may be used. Polymerization catalysts are those compounds which increase the rate of polymerization by promoting decomposition of the free radical initiator in combination with the reducing agent at the reaction conditions. Suitable catalysts include transition metal compounds such as, for example, ferrous sulfate heptahydrate, ferrous chloride, cupric sulfate, cupric chloride, cobalt acetate, cobaltous sulfate, and mixtures thereof.

In addition, a low level of a chain transfer agent may also be used to prepare a polymer in accordance with the invention. Suitable chain transfer agents include, but are not limited to, butyl mercaptan, n-octylmercaptan, n-dodecyl mercaptan, butyl or methyl mercaptopropionate, mercaptopropionic acid, 2-ethylhexyl 3-mercaptopropionate, n-butyl 3-mercaptopropionate, isodecylmercaptan, octadecylmercaptan, mercaptoacetic acid, haloalkyl compounds, (such as carbon tetrabromide and bromodichloromethane), and the reactive chain transfer agents described in U.S. Pat. No. 5,247,040, incorporated herein by reference. In particular, mercaptopropionate, allyl mercaptopropionate, allyl mercaptoacetate, crotyl mercaptopropionate and crotyl mercaptoacetate, and mixtures thereof, represent preferred chain transfer agents.

A copolymerizable monomer known to promote wet adhesion may also be incorporated into the polymer. Examples of wet adhesion promoting monomers include, but are not limited to, nitrogen-containing monomers such as t-butylaminoethyl methacrylate, dimethylaminoethyl methacrylate, diethylaminoethyl methacrylate, N,N-dimethylaminopropyl methacrylamide, 2-t-butylaminoethyl methacrylate, N,N-dimethylaminoethyl acrylate and N-(2-methacryloyloxyethyl)ethylene urea.

Water-dispersible and water-soluble polymers may also be employed as surfactants or stabilizers in accordance with the present invention. Examples of such polymeric stabilizers include water-dispersible polyesters as described in U.S. Pat. Nos. 4,946,932 and 4,939,233; water-dispersible polyurethanes as described in U.S. Pat. Nos. 4,927,876 and 5,137,961; and alkali-soluble acrylic resins as described in U.S. Pat. No. 4,839,413, all of which are incorporated herein by reference. Cellulosics and polyvinyl alcohols may also be used. Surfactants and stabilizers may be used during the polymerization to control, for example, particle nucleation and growth, particle size and stability or they may be post added to enhance stability of the latex or modify other properties of the latex such as surface tension, wettability and the like.

In an embodiment, at least one ethylenically unsaturated copolymerizable surfactant may be employed, for example those possessing isopropenyl phenyl or allyl groups. Copolymerizable surfactants may be anionic, such as containing a sulfate or sulfonate group, or nonionic surfactants. Other copolymerizable surfactants include those containing polyoxyethylene alkyl phenyl ether moieties. Additional copolymerizable surfactants include sodium alkyl allyl sulfosuccinate.

The latex polymers in accordance with the invention may have a weight average molecular weight (Mw), for example, of from 1,000 to 1,000,000, as determined by gel permeation chromatography (GPC), or from 5,000 to 250,000.

The particle size for the aqueous dispersions in accordance with the invention may be, for example from about 0.01 to about 25 μm, or from 0.05 to 1 μm, or from 0.075 to 500 μm. Thus, in an emulsion polymerization in accordance with the invention, the particle size of the latex may range, for example, from about 0.01 to 5 μm. On the other hand, in a suspension polymerization in accordance with the invention, the latex particle size may range, for example, from 2 to 25 μm, or from 3 to 20 μm, or from 4 to 15 μm.

The latex particles generally have a spherical shape, and the spherical polymeric particles may have a core portion and a shell portion or a gradient structure. The core/shell polymer particles may also be prepared in a multi-lobe form, a peanut shell, an acorn form, a raspberry form or any other form. If the particles have a core/shell structure, the core portion may comprise from about 20 to about 80 wt % of the total weight of the particle, and the shell portion may comprise about 80 to about 20 wt % of the total weight of the particle.

The glass transition temperature (Tg) of the latex polymers in accordance with the present invention, may be up to about 100° C. In a preferred embodiment of the present invention, where a film forming at ambient temperatures of the particles is desirable, the glass transition temperature may preferably be under 60 C.

The latex polymers of the invention may comprise enamine functional polymers, with the enamine functionality serving to improve the hydrolytic stability of the acetoacetoxy group. Enamine functional polymers have been described in Polymer Bulletin 32, 419-426 (1994). Additionally, enamine functional polymers are described in European Patent Application No. 0492847 A2; U.S. Pat. No. 5,296,530; and U.S. Pat. No. 5,484,849, all of which are incorporated herein by reference.

A latex polymer formed from the inventive monomers of the invention may likewise be, for example, the emulsion polymerization product of:

(i) from about 0.5 to about 30 wt % of one or more acetoacetate-functional monomers, or from 2 to 25 wt %, or from 5 to 20 wt %;

(ii) from 0 to about 6 wt % of a carboxylic acid-functional vinyl monomer, with a preferred range of about 0.5 to about 4 wt %; and (iii) from about 40 to about 99.5 wt % of additional monomers that are non-acid, and that are not acetoacetate-functional monomers, alternatively from 60 to 99 wt %.

A latex polymer of the invention containing residues from the acetoacetate-functional monomers of the invention may also contain (iv) about 0.5 to about 5 wt % of a non-self polymerizing, surface-active vinyl monomer, preferably about 1.0 to about 3.0 wt %, and (v) about 0.1 to about 10 wt % of an adhesion-promoting monomer. The wt % is based on the total amount of monomer.

The acid-functional vinyl monomers used may be selected broadly from carboxylic acids, phosphonic acids, acid anhydrides, phosphate monomers, and other functionalities which are capable of reacting with a base to form a salt. Examples of suitable carboxylic acid-functional vinyl monomers, or vinyl monomers capable of providing carboxylic acid-functionality, include, but are not limited to, acrylic acid, methacrylic acid, itaconic acid, itaconic anhydride, citraconic acid, citraconic anhydride, and maleic anhydride. Acrylic acid, methacrylic acid, itaconic acid and maleic anhydride represent preferred carboxylic acid-functional monomers, or monomers capable of providing carboxylic acid-functionality.

Specific examples of suitable vinyl monomers that are not acids, and that are not acetoacetate-functional monomers, include, but are not limited to, methyl(meth)acrylate, ethyl(meth)acrylate, butyl(meth)acrylate, hexyl(methacrylate), isooctyl(methacrylate), isodecyl(meth)acrylate, lauryl(meth)acrylate, stearyl(meth)acrylate, phenoxyethyl(meth)acrylate, methoxyethyl(meth)acrylate, benzyl(meth)acrylate, furyl(meth)acrylate, methylfuryl(meth)acrylate, butylfuryl(meth)acrylate, tetrahydrofuryl(meth)acrylate, ethoxyethyl(meth)acrylate, 2-ethylhexyl(meth)acrylate, cyclopentyl(meth)acrylate, isobornyl(meth)acrylate, hydroxyethyl(meth)acrylate, hydroxypropyl(meth)acrylate, and combinations or mixtures thereof. Others include styrene derivatives and vinyl derivatives. Examples of suitable styrene derivatives include, but are not limited to, styrene, vinyl toluene, o-methyl styrene, p-methyl styrene and m-methyl styrene. Vinyl derivatives include, but are not limited to, vinyl esters such as vinyl acetate, vinyl propionate, vinyl 2-ethylhexanoate, vinyl neononoate, vinyl neodecanoate, and vinyl esters of versatic acid. Such monomers are described in The Brandon Worldwide Monomer Reference Guide and Sourcebook, Second Edition, 1992, Brandon Associates, Merrimack, N.H.; and in Polymers and Monomers, the 1996-1997 Catalog from Polyscience, Inc., Warrington, Pa.

The latexes formed may optionally be combined with an amine or with a poly(alkylenimine). Blending the acetoacetoxy-functional polymer with a poly(alkylenimine) has the advantage of imparting solvent resistance to the water-based coating composition, providing excellent hardness, gloss, gloss retention, solvent and chemical resistance, and weathering, without compromising anti-corrosion performance. Application of the coating composition to a substrate prompts crosslinking within the film composition through dehydration and resulting enamine formation through reaction of the acetoacetoxy moieties on the acetoacetoxy-functional polymer with the poly(alkylenimine). Such a coating composition may be formulated as a one-pack composition containing the blended latex, or as a two-pack system where the latex and the poly(alkylenimine) are blended prior to use.

A latex composition of the invention may be prepared by free radical emulsion polymerization of one or more acetoacetate-functional monomers such as those represented by formula 1 above, optionally with carboxylic acid-functional vinyl monomers, and with non-acid, non-acetoacetoxy vinyl monomers. The polymerization reaction affords a water-based dispersion of polymer particles with the polymer having pendant acetoacetate-functional groups. A pendant acetoacetate-functional group is not limited to those at the termini of the polymer. Pendant acetoacetoxy groups also include groups attached to the polymer's backbone and available for further reaction.

In one aspect, the invention is thus directed to latex formulations containing a polymeric ingredient having at least acetoacetate-functional pendant moieties derived from the unsaturated acetoacetate-functional monomers of formula 1 dispersed in an evaporable aqueous carrier. The acetoacetate-functional moiety employed in the polymers and latex formulations of this invention advantageously exhibit excellent hydrolytic stability so that such formulations can be stored for long periods of time without degradation of the acetoacetate-functionality. Additionally, the acetoacetate-functional moiety employed in the polymers and latex formulations of this invention advantageously exhibit the ability to crosslink via a self-curing "oxidative cure", react with an added cross-linker such as a diamine, or cure using ultraviolet light with or without the addition of photoinitiators.

Preferred examples of the monomers are 3-(methacryloyloxy)-2,2-dimethylpropyl 3-oxobutanoate, 3-(methacryloyloxy)-2,2,4,4-tetramethylcyclobutyl 3-oxobutanoate, either of the following two isomers, 3-(methacryloyloxy)-2,2,4-trimethylpentyl 3-oxobutanoate or 1-(methacryloyloxy)-2,2,4-trimethylpentan-3-yl 3-oxobutanoate or mixtures thereof, and (4-(methacryloyloxymethyl)cyclohexyl)methyl 3-oxobutanoate, corresponding to the following structures:

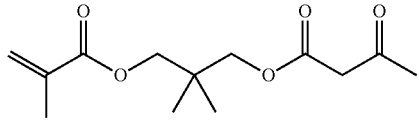
(2)

-continued

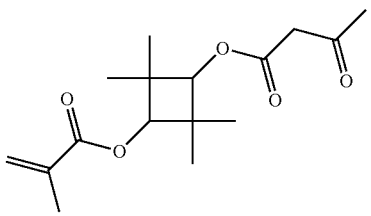
(3)

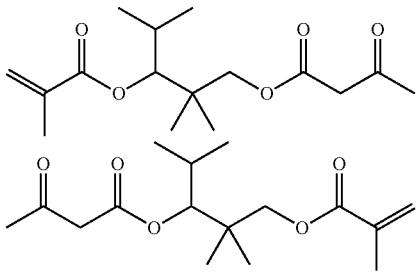
(4)

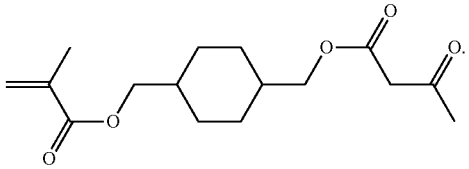
(5)

Solution Polymers Made from the Ethylenically Unsaturated Acetoacetate-Functional Monomers In another aspect, the acetoacetate-functional monomers may be used to form homopolymers, or copolymers with the other ethylenically unsaturated monomers already described, as solution polymers. Solution polymers are addition polymers, as are the latexes or emulsion polymers just described, but are polymerized by dissolving the monomer(s) typically in a non-reactive solvent that contains a catalyst. The heat produced by the polymerization reaction is absorbed by the solvent, thus controlling the reaction rate. These solution polymers may be formed from the same ethylenically unsaturated monomers already described above with respect to suspension and emulsion polymers, and their preparation is well known to those skilled in the art of polymerization.

Simple Mixtures of Ethylenically Unsaturated Acetoacetate-Functional Monomers, and Optionally Other Ethylenically Unsaturated Monomers, as Coating Compositions The ethylenically unsaturated acetoacetate-functional monomers of the invention may be used, alone or with other ethylenically unsaturated monomers, as coating compositions that, when applied to a substrate, form polymers to provide a coating layer on the substrate. These mixtures may be used with a photoinitiator, since the reaction may not be a self-polymerization. For this use, also, the hydrolytic stability of the inventive monomers is a desirable feature, since the monomers will exhibit improved hydrolytic stability during storage, rather than breaking down to the decomposition products as described below with respect to AAEM.

EXAMPLES

The following examples are given to illustrate the invention. It should be understood, however, that the invention is not to be limited to the specific conditions or details described in these examples.

Example 1

Preparation of 3-(methacryloyloxy)-2,2-dimethylpropyl 3-oxobutanoate

To a 2-L flask was charged neopentyl glycol (208.3 g, 2.0 moles), toluene (250 mL), hydroquinone (0.5 g) and sodium methoxide (25% in methanol, 8 g). The mixture was heated to 60-65° C. and methyl methacrylate (120 g, 1.2 moles) was added dropwise over 1 hour. The reaction was held at 70° C. for one hour under moderate vacuum to remove methanol and low boilers. Reaction was worked up by washing with 2×250 mL water and 1×100 mL saturated sodium chloride solution at 70° C. Toluene was evaporated and the resulting crude product (166 g) distilled to provide 3-hydroxy-2,2-dimethylpropyl methacrylate of 97% GC assay. To a 300 mL flask was charged 3-hydroxy-2,2-dimethylpropyl methacrylate (11.5 g, 0.064 moles), methylene chloride (20 g), DMAP (0.01 g), hydroquinone (0.05 g) and the mixture cooled to 0-5° C. To this was added dropwise diketene (5.4 g) at <3° C. Reaction allowed to warm to room temperature and stir overnight. Reaction cooled to 0-5° C. and additional diketene (2 g) added to complete reaction. Once reaction was complete, the dichloromethane was removed at 60° C. with house vacuum. Crude product distilled via Kugelrohr distillation to provide desired product of 92.6% assay with 1.6% starting material remaining (GC assay).

Example 2

Preparation of 3-(methacryloyloxy)-2,2,4,4-tetramethylcyclobutyl 3-oxobutanoate To a 3-L flask was charged 2,2,4,4-tetramethylcyclobutane-1,3-diol (423.26 g, 3.0 moles), THF (550 g), DMAP (0.5 g) and N-diphenylnitrosoamine (2 g) and methacrylic anhydride (308 g, 2 moles). Mixture heated to reflux (81° C.) and held for six hours. Reaction cooled and THF removed with a rotary evaporated. To the crude residue was added heptane (1200 mL) and cooled to 0-5° C. for 30 minutes. The precipitated unreacted starting material was filtered off and the cake washed with cold heptanes (600 mL). Heptane removed from filtrate with rotary evaporator and the crude product distilled through a 12×1 inch Penn State packed column to produce 3-hydroxy-2,2,4,4-tetramethylcyclobutyl methacrylate in 97.3% NMR assay. To a 500 mL flask was charged 3-hydroxy-2,2,4,4-tetramethylcyclobutyl methacrylate (32 g, 0.151 moles), methylene chloride (75 g), DMAP (0.04 g) and the mixture cooled to 0-5° C. To this was added dropwise over one hour freshly distilled diketene (12.7 g) dissolved in methylene chloride (20 g). After addition, the reaction was allowed to warm to room temperature and stir overnight. Once reaction was complete, the dichloromethane was removed at 60° C. with house vacuum. Crude product distilled via Kugelrohr distillation to provide desired product of 94.8% GC assay.

Example 3

Preparation of a mixture of 3-(methacryloyloxy)-2,2,4-trimethylpentyl 3-oxobutanoate and 1-(methacryloyloxy)-2,2,4-trimethylpentan-3-yl 3-oxobutanoate To a 1-L flask was charged 2,2,4-trimethyl-1,3-pentanediol (146.2 g, 1.0 moles), THF (100 grams) DMAP (0.2 g) and methacrylic anhydride (77.1 g, 0.5 moles). The batch was refluxed and held until complete by GC (3 hrs). The reaction was cooled and THF and methacrylic acid removed with a rotary evaporator. Acetone (300 mL) and p-toluenesulfonic acid (0.5 g) was added to the residue. The reaction was heated to reflux and the distillate allowed to pass through 4 angstrom molecular sieves for approximately 3 hours to convert the unreacted 2,2,4-trimethyl-1,3-pentanediol to its ketal derivative. N-Diphenylnitrosoamine was added and the ketal derivative was removed by rotary evaporator at 85-90° C. (0.5 mmHg). The desired mono-hydroxy-2,2,4-trimethylpentyl methacrylate was isolated from the dimethacrylate by-product by Kugelrohr distillation. The isolated yield was approximately 50% and assayed 90% by GC. To a 250 mL flask was charged mono-hydroxy-2,2,4-trimethylpentyl methacrylate (10.7 g, 0.5 mol), methylene chloride (50 g) and DMAP (0.1 g) and the mixture cooled to <10° C. Diketene (4.6 g) and methylene chloride (20 g) were mixed and added at <10° C. When the addition of diketene was complete the batch was allowed to warm to ambient temperature. The methylene chloride was removed under vacuum with a rotary evaporator to provide the desired products in 90% assay (GC).

Comparative Example 1

Acetoacetoxyethyl Methacrylate (AAEM)

AAEM available from Eastman Chemical Company was used as a control in Comparative Example 1.

Example 6

Accelerated Hydrolysis Testing of 1,3-Diketo Monomers

The predominant mode of decomposition for 1,3-diketo species is loss of the acetoacetyl group via formation of acetone and carbon dioxide as shown in Equation 1.

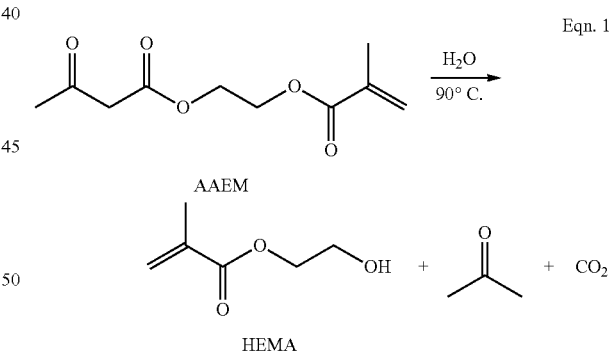

It is possible to monitor this decomposition by either HPLC analysis of the starting materials and decomposition products (AAEM and HEMA in Eqn. 1) or by GC analysis of the acetone.

To evaluate the monomers in a reasonable length of time, an accelerated hydrolysis test was used to evaluate the hydrolytic stability of the new monomers. A solution of 0.5% of the monomer in water was held at 90° C. and samples analyzed by HPLC over time. The disappearance of the starting monomer and the concurrent appearance of hydrolysis products can thus be determined and related to the hydrolytic stability of the monomer. In general, the less decomposition seen, the more hydrolytically stable the monomer is.

TABLE 1

Accelerated Hydrolysis Testing of Monomers

| Time (hr) | % Monomer Remaining | | | |
|---|---|---|---|---|
| | Example 1 | Example 2 | Example 3 | Comparative Example 1 |
| 0 | 91.3 | 88.3 | 67.3 | 97.7 |
| 1 | 85.3 | | | 96.1 |
| 2 | 79.8 | | | 94.1 |
| 3 | 74.7 | 79.9 | 66.6 | 91.4 |
| 4 | 70.9 | | | |
| 5 | | 76.9 | 65.7 | 85.0 |
| 7 | | 67.5 | 65.9 | |
| 8 | | | | 77.9 |
| 24 | 54.1 | 46.2 | 52.8 | 43.2 |
| 30 | | | | 35.1 |
| 48 | 43.2 | 32.6 | 42.4 | 9.8 |
| 54 | | 24.3 | 34.5 | 7.8 |
| 72 | 33.9 | 18.5 | 36.3 | |
| 96 | 22.0 | 12.1 | 26.6 | |

As demonstrated in Table 1, the sterically hindered acetoacetate containing monomers exemplified by Examples 1-3 were more hydrolytically stable than AAEM (Comparative Example 1).

Water-Based Latexes

In general, and as further described above, water-based latexes of the invention may be prepared by polymerizing acrylic (ethylenically unsaturated) monomers in the presence of the acetoacetate-functional monomers of the invention. Before conducting polymerization, these ethylenically unsaturated monomers are either pre-emulsified in water/surfactant mixture or used as such.

The polymerization process of making these 'acrylic' latexes may also require an initiator (oxidant), a reducing agent, or a catalyst. Suitable initiators include conventional initiators such as ammonium persulfate, sodium persulfate, hydrogen peroxide, t-butyl hydroperoxide, ammonium or alkali sulfate, di-benzoyl peroxide, lauryl peroxide, di-tertiarybutylperoxide, 2,2-azobisisobutyronitrile, benzoyl peroxide, and the like.

Suitable reducing agents are those which increase the rate of polymerization and include, for example, sodium bisulfite, sodium hydrosulfite, sodium formaldehyde sulfoxylate, ascorbic acid, isoascorbic acid, and mixtures thereof.

Suitable catalysts are those compounds which promote decomposition of the polymerization initiator under the polymerization reaction conditions thereby increasing the rate of polymerization. Suitable catalysts include transition metal compounds and driers. Examples of such catalysts include, but are not limited to, AQUACAT™, ferrous sulfate heptahydrate, ferrous chloride, cupric sulfate, cupric chloride, cobalt acetate, cobaltous sulfate, and mixtures thereof.

A conventional surfactant or a combination of surfactants is used as a stabilizer, such as an anionic or non-ionic emulsifier, in the suspension or emulsion polymerization preparation of a hybrid latex of the invention. Examples of preferred surfactants include, but are not limited to, alkali or ammonium alkylsulfate, alkylsulfonic acid, or fatty acid, oxyethylated alkyphenol, sulfosuccinates and derivatives, or any combination of anionic or non-ionic surfactants. A list of suitable surfactants is available in the treatise: McCutcheon's Emulsifiers & Detergents, North American Edition, MC Publishing Co., Glen Rock, N.J., 1997. Preferably, the surfactant will provide droplet/particle stability, but result in minimal aqueous phase nucleation (micellar or homogeneous).

We claim:

1. An acetoacetate-functional monomer corresponding to one of the following structures (2) through (5):

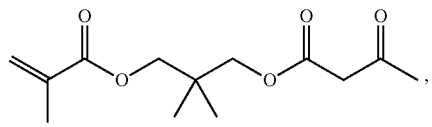

(2)

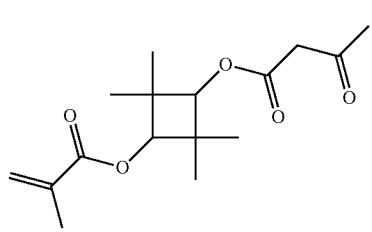

(3)

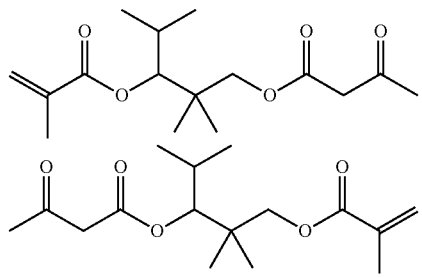

(4)

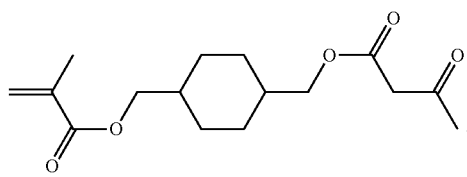

, and (5)

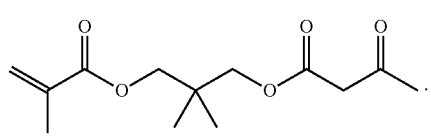

.

2. The acetoacetate-functional monomer of claim 1, wherein the monomer corresponds to the following structure:

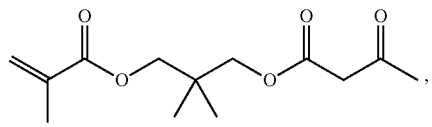

(2)

.

3. The acetoacetate-functional monomer of claim 1, wherein the monomer corresponds to the following structure:

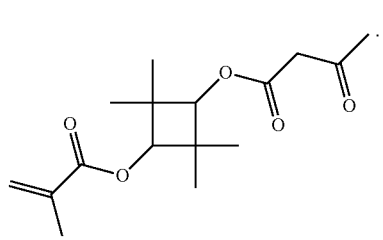

(3)

.

4. The acetoacetate-functional monomer of claim 1, wherein the monomer corresponds to either of the following two isomers, or mixtures thereof:

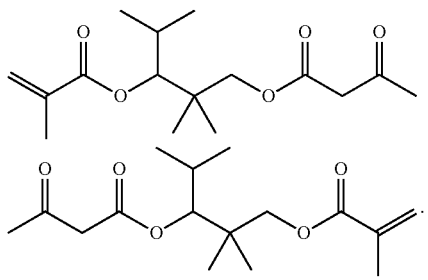
(4)

5. The acetoacetate-functional monomer of claim 1, wherein the monomer corresponds to the following structure:

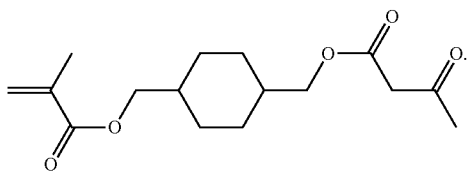
(5)

6. An emulsion polymer comprising residues from the acetoacetate-functional monomer of claim 1 and one or more additional ethylenically unsaturated monomers.

7. The emulsion polymer of claim 6, where the one or more additional ethylenically unsaturated monomers comprise one or more of: methyl(meth)acrylate, ethyl(meth)acrylate, propyl(meth)acrylate, isopropyl(meth)acrylate, butyl(meth)acrylate, isobutyl(meth)acrylate, hexyl(meth)acrylate, isooctyl(meth)acrylate, isodecyl(meth)acrylate, lauryl(meth)acrylate, stearyl(meth)acrylate, phenoxyethyl(meth)acrylate, methoxyethyl(meth)acrylate, benzyl(meth)acrylate, ethoxyethyl(meth)acrylate, 2-ethylhexyl(meth)acrylate, cyclopentyl(meth)acrylate, isobutyl(meth)acrylate, styrene, p-methyl styrene, o-methyl styrene, p-butyl styrene, or alpha-methyl styrene.

8. A solution polymer comprising residues from the acetoacetate-functional monomer of claim 1.

9. A self-curing coating composition comprising the acetoacetate-functional monomer of claim 1, and optionally one or more additional ethylenically unsaturated monomers.

10. A latex formulation comprising a polymer having residues from the acetoacetate-functional monomer of claim 1 dispersed in an aqueous carrier.

* * * * *